United States Patent [19]

Hiroyoshi

[11] Patent Number: 4,678,468

[45] Date of Patent: Jul. 7, 1987

[54] CARDIOVASCULAR PROSTHESIS

[75] Inventor: Toshiki Hiroyoshi, Yao, Japan

[73] Assignee: Bio-Medical Co., Ltd., Japan

[21] Appl. No.: 762,168

[22] Filed: Aug. 5, 1985

[30] Foreign Application Priority Data

Aug. 7, 1984 [JP] Japan ................................ 59-165090

[51] Int. Cl.$^4$ .............................................. A61F 2/06
[52] U.S. Cl. ...................................................... 623/1
[58] Field of Search ............................................ 623/1

[56] References Cited

U.S. PATENT DOCUMENTS

| | | | |
|---|---|---|---|
| 3,327,705 | 6/1967 | Miller et al. ........................ | 128/165 |
| 4,189,546 | 2/1980 | Deichert ................................ | 623/1 |
| 4,208,506 | 6/1980 | Deichert ................................ | 623/1 |
| 4,219,520 | 8/1980 | Kline ..................................... | 623/1 |
| 4,254,180 | 3/1981 | Kline ..................................... | 623/1 |

Primary Examiner—Gregory E. McNeill
Attorney, Agent, or Firm—Armstrong, Nikaido, Marmelstein & Kubovcik

[57] ABSTRACT

In a cardiovascular prosthesis, at least a part of blood contact surface of the prosthesis is formed by polymer composition comprising water soluble polymer such as heparin and crosslinked polysiloxane, at least a part of the water soluble polymer being entangled or intertwisted into polysiloxane networks.

11 Claims, No Drawings

CARDIOVASCULAR PROSTHESIS

BACKGROUND OF THE INVENTION

1. Field of the invention

The present invention relates to a cardiovascular prosthesis with excellent patency or biocompatibility, especially a vascular graft of medium or small diameter, and a method of producing the same.

2. Description of the Prior Art

Vascular surgeries are performed to reconstruct or repair damaged vessels by replacing the damaged portions with vascular grafts or other prostheses. There have been a number of developments aiming at the replacement of the damaged areas by using suitable conduits or making bypasses beyond the damaged areas or reconstruction a new route where no neutral vessels previously existed.

The critical problem facing patients and surgeons alike is to find a suitable conduit. Key to the success for being acceptable by patient body has been found that the implanted material should have pertinent porous structure to help the ingrowth of endothelial cells. Accordingly, vascular protheses made of flexible materials with porous structures have been used. Porousness is usually expressed by water permeability at a certain condition.

Porous structure of the graft accelerates the formation of a thin blood coagulanting layer along the inner surface of the graft, and helps the ingrowth of the endothelial cells. Generally, favorable dimension of the porous structure ranges between $1\mu$ and $100\mu$.

So far, fabric or woven conduit made of polyethylene terephthalate or expanded polytetrafluoroethylene (EPTFE) tube have met these requirements have been practically used worldwide for this purpose.

SUMMARY OF THE INVENTION

An object of this invention is to provide a cardiovascular prosthesis wherein at least a part of the blood contact surface is formed by polymer composition comprising water soluble polymer and crosslinked polysiloxane, at least a part of said water soluble polymer being entangled or intertwisted into polysiloxane networks.

A further object of this invention is to provide a cardiovascular prosthesis wherein at least a part of the blood contact surface is composed of heparin together with other kinds of water soluble polymer and crosslinked polysiloxane, at least a part of heparin and said other water soluble polymer being entangled or intertwisted into polysiloxane networks.

A still further object of this invention is to provide a cardiovascular prosthesis wherein at least a part of the blood contact surface is formed by polymer composition comprising heparin and polyvinyl alcohol as essential ingredients along with other kinds of water soluble polymer and cross-linked polysiloxane, at least a part of heparin and the other water soluble polymer being entangled or intertwisted into polysiloxane networks.

Still a further object of this invention is to provide a method of producing a cardiovascular prosthesis which comprises a treatment of cardiovascular prosthesis body with a solution containing water soluble polymer and silico-component which is capable of inducing polymerization to a crosslinked polysiloxane.

DESCRIPTION OF THE PREFERRED EMBODIMENTS

A study of the current scientific and medical literature reveals that satisfactory synthetic grafts are available on the market for replacing large diameter arteries. In the area of small diameter arterial repair, however, vascular grafts have not been accepted because of prompt occlusion after implantation. Thus, in the area of smaller diameter arterial repair, the autogeneous saphenous vein which is harvested from the patient's leg remains as the conduit of choice.

When such a synthetic graft is implanted by replacing the damaged portion of the artery, almost immediately the inner surface of the graft is covered with a layer of the blood-coagulating material. The thickness of the layer depends on the properties of the surface such as kind of material, surface structure and so on. The thickness of the coagulating layer is usually up to 0.5 to 1.0 mm. A vascular graft of over 10 mm diameter has practically little trouble in repairing the damaged artery, however, vascular grafts of intermediate diameter ranged 10 to 7 mm are always facing trouble of narrowing in diameter and that long term patencies are not so satisfactory. It has been known that venous repair is more difficult than arterial repair, and there has been no graft usable for venous replacement on the market. Even for arterial repair, there has been practically no graft acceptable for smaller diameter than 6 mm.

Requirements for acceptance as vascular prostheses are as follows:

(1) non-toxicity;
(2) no unfavorable bioreaction;
(3) long-term durability with no deterioration;
(4) pertinent elasticity and compliance;
(5) anti-coagulant property;
(6) biolizable nature;
(7) good suturability;
(8) little or no blood leakage;
(9) sterilizability; and
(10) possible various designs.

Among these, longtime patency is most important.

The present inventor has found the way to develop medium and small size vascular grafts with longterm patencies, which may also be applicable for venous repair. At the same time, the method can apply for large diameter vascular graft for which better patency rate and longer durability may be achieved than the current ones on the market.

The present invention is characterized in that at least a part of the blood-contact surface of the vascular graft is formed by a polymeric composition in which water soluble polymer is entangled or intertwisted into polysiloxane chain networks to form interpenetrating polymer networks (IPN).

Briefly describing, this invention can be performed by treating the graft with an aqueous sol-like solution containing water soluble polymer and silicon containing substance which can polymerize through condensation reaction to form cross-linked polysiloxane.

An object of this invention is to provide a cardiovascular prosthesis whose blood contact surface are formed by a polymer composition comprising water soluble polymer and polysiloxane, where the water soluble polymer is entangled into polysiloxane polymer networks. The water soluble polymer may include at least one of the materials selected from the group which comprises heparin, polyethyleneglycol, polypropylene glycol, ethylene oxide-propylene oxide random copolymer or block copolymer of A-B type, and A-B-A type, polyvinyl pyrrolidone, soluble collagen (Atelo colagen; trade name), gelatin, polyacrylic acid, polymethacrylic acid, or their derivatives such as polyhydroxyethyl methacrylic acid, polyacrylamide, polymethacrylamide, and polyvinyl alcohol, 2-acrylamide-2-methyl propane sulfonic acid, diacetone acrylamide alginic acid, soluble-starch, methylcellulose, polysaccharide of any kinds such as hyaluronic acid, chondroitin sulphate, oxidized-starch or dialdehyde starch.

Another object of this invention is to provide a cardiovascular prosthesis whose blood contact surface is composed of heparin as an essential ingredient together with other one or more kinds of water soluble polymer and crosslinked polysiloxane, wherein at least a part of heparin and the other water soluble polymer are entangled or intertwisted into polysiloxane polymer networks to form IPN.

Still another object of this invention is to provide a cardiovascular prosthesis whose blood contact surface is formed by a polymer composition comprising heparin and polyvinyl alcohol as essential ingredients along with the other kinds of water soluble polymer and crosslinked polysiloxane, wherein at least a part of heparin and the other water soluble polymer are entangled into polysiloxane polymer networks.

One of the biggest problems for the practical application of small diameter vascular graft is the occlusion before its biolization through endothelial lining.

To prevent this occlusion, treatment with heparin aqueous solution, or treatment with tertiary amine heparin complex has been attempted so far, however, it becomes apparent in both cases, that heparin run short in very early period.

Attempts to incorporate heparin molecule into the surface with covalent bond seem unsuccessful, because any chemical modification reduces its anticoagulant activity remarkably.

Nagata and Iyota proposed an interesting method for incorporating heparin molecule into the surface. They used polydimethylsiloxane and heparin-tertiary ammonium complex salt.

They utilized the fact that heparin can be converted into a soluble material in dichloromethane by forming quarternary ammonium complex. Thus, polydimethylsiloxane and heparin-quartery ammonium complex are dissolved in dichloromethane, then, the mixture subsequently allowed to react with silane-coupling agent. They described heparin molecules are chemically bonded via oxygen (Si-O-Heparin) onto polydimethylsiloxane by this reaction. As already described, as long as this reaction involves the chemical modification of heparin, its original anticoagulant property can not be expected.

The present inventor finally found a new method after intensive studies, by which initial blood coagulant layer after implantation of the graft is controlled to a much thinner lining which also effects to make the subsequent endothelial thickness significantly reduced.

The present invention relates to a cardiovascular prosthesis wherein at least a part of blood-contact surface is formed by a polymer composition comprising water soluble polymer entangled into or intertwisted into crosslinked polysiloxane network to form IPN (Interpenetrating polymer networks: L. H. Sperling, Encyclopedia Polymer Science and Technology, Supplement Vol. 1, 288, 1976, Interscience Publisher, New York).

In order to make IPN, it is essential that polymerization to polysiloxane, which accompanies crosslinking reactions, should proceed under the condition that polymerizable silicon-containing materials should be completely soluble or homogeneously mixed in the reaction medium. In this point, the method proposed by Nagata and Iyota is not so pertinent because they used polymeric polysiloxane, as a component. It is well-known that two or more polymeric materials can not mixed homogeneously with each other in the common solvent, but they form a mixture of small aggregates of the same kind of polymer molecules to form "apparent" solution with microphase separation.

Accordingly, in order to form interpenetrating polymer networks, the polymerizable silicon-containing substance should be an monomeric or at least should be oligomer which undergoes polymerization accompanying crosslinking reactions.

The following is the description of this invention in more details.

The method to achieve this invention is as follows.

The solutions for treating cardiovascular prostheses such as vascular prosthesis or cardiac prostheses are aqueous or water-containing solutions (hereafter we call IPN solution). The silicon-containing component should contain crosslinkable ingredient (hereafter called silico-crosslinking agent) with more than three functional sites capable for polymerization (for example, —OH group).

It should be emphasized the silicon-containing component used in this invention should be monomeric or at least in the form of oligomer of low molecular weight. Thus, silicon-containing component (hereafter we call silico-component) should include silico-crosslinking agent.

As silico-crosslinking agent, usual silan-coupling agent used for room temperature vulcanization (RTV) for silicone resin can be widely used.

Among the silico-crosslinking agent, those of water activated are favorably used.

Typical functional group are ≡Si—O—COR, ≡SiOR (where R is hydrocarbon radical like $CH_3$, $C_2H_5$, $C_3H_7$, $C_4H_9$, etc), ≡SiOX, ≡SiX (X is halogen like Cl, Br, etc.), Si—$NR_2$ (R is the same as above). The silico-crosslinking agent gives polysiloxane after polymerization.

Silico-crosslinking agents having one silicon atom in the molecule, which liberate functional sites by the action of water, are shown in the following formula (1):

$$R_nSiR'_{4-n} \tag{1}$$

where R is hydrocarbon radical like alkyl, aryl, R' is alkoxy, acyloxy, halogen, or amine-radical, and n=0 or 1.

Examples are tetraacetoxy silane, methyltriacetoxy silane, ethyltriacetoxy silane, propyltriacetoxy silane, butyltriacetoxy silane, phenyltriacetoxy silane, methyltriethoxy silane, ethyltriethoxy silane, tetraethoxy silane, phenyltriethoxy silane, propyltriethoxy silane, butyltriethoxy silane, methyltrimethoxy silane, tetramethoxy silane, ethyltrimethoxy silane, propyltrimethoxy silane, butyltrimethoxy silane, tetrachloro silane, methyltrichloro silane, ethyltrichloro silane, butyltrichloro silane, vinyltriacetoxy silane, bis-(N-methylbenzylamido)ethoxymethyl silan, tris-(dimethylamino)- methyl silan, vinyltrichlro silane, tris-(cyclohexylamino)methyl silane, vinyltriethoxy silane, α-glycidoxypropyl-trimethoxy silane, tetrapropoxy silane divinyldiethoxy silane. Silico-crosslinking agent having two silicon atoms in molecule is shown in the following formula (2):

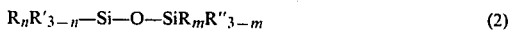

$$R_nR'_{3-n}—Si—O—SiR_mR''_{3-m} \quad (2)$$

(wherein n or m=0, 1, 2 or 3, n+m=0, 1, 2 or 3, R is hydrocarbon radical with no crosslinking capability, and each of R' and R'' is one of the group capable of converting to a functional group for polymerization by activation; called functional group as before). Examples are hexaacetoxy disiloxane; 1,3-dimethyltetraacetoxy disiloxane; and 1,3-divinyl tetraethoxy disiloxane. The examples of silico-crosslinking agent having three silicon atoms in molecule are 1,3,5-trimethoxy-1,1,5,5-pentamethyl trisiloxane; 1,1,3,3,5,5-hexaacetoxy-1,5-methyltrisiloxane and so on. Silico-crosslinking agents are described in the catalogue, Silicon cumpound, Register and Review by Petrarch System, Inc.

In addition to silico-crosslinking agent, bi-functional silico-components which induce condensation polymerization to form polysiloxane can be used. This type of silico-compound is expressed in the following formula (3):

$$\begin{array}{c} R_1 \quad R_3 \\ | \quad | \\ Y—Si\!\!-\!\!(O—Si)_n\!\!-\!\!Y' \\ | \quad | \\ R_2 \quad R_4 \end{array} \quad (3)$$

where $R_1$ to $R_4$ are same or different hydrocarbon radical, n=0, 1, 3, ..., and Y and Y' are same or different group which can be converted to functional groups by activater like $H_2O$, capable of polymerization to form polysiloxane. The examples of this type are silico-compounds in which two hydrocarbon and two-functional radical attached to a silicon atom, that is, dimethyl diacetoxy silane, diethyl diacetoxy silane, dimethyl diethoxy silane, diethyl diethoxy silane, methyl ethyl dimethoxy silane, diethyl dimethoxy silane, dimethyl dichloro silane, methyl phenyl diacetoxy silane, diphenyl diacetoxy silane, dibenzyl diacetoxy silane, divinyl diethoxy silane. In addition to these, 1,1,3,3-tetramethyl-1,3-diacetoxy disiloxane; 1,1,3,3-tetramethyl-1,3-dimethoxy disiloxane; 1,1,3,3-trtraethyl-1,3-diethoxy disiloxane; 1,1,3,3,5,5-hexamethyl-1,5-diacetoxy trisiloxane; 1,1,3,3,5,5-hexaethyl-1,5-diethoxy trisiloxane; 1,1,3,3,5,5-hexamethyl-1,5-dimethoxy trisiloxane; 1,1,1,5,5,5-hexamethyl-3,3-diacetoxy trisiloxane; 1,1,1,3,5,5-hexamethyl-3,5-diacetoxy trisiloxane are examples of bifunctional silicon component. Bifunctional silico-component is also expressed in formula (1) with n=3, and formular (2) with n+m=b 4

In the practical use of this invention, the solution for treatment (IPN solution) is first prepared. The water soluble polymer is firstly dissolved in water or in water containing solvent to make homogeneous solution. To this, the silico-component mentioned above is then added. The order of the addition is very important. If the order is reverse, that is, the water soluble polymer is added in the last place, silico-components already undergo polycondensation reaction to some extent to form polysiloxane of rather high molecular weight. In this case, microphase separation between resultant polysiloxane and the water soluble polymer may develop and hence there is rather little chance for water soluble polymer to intertwist into crosslinking networks of polysiloxane, thus, IPN is not nicely formed.

If the addition order is right, monomeric silanol compound derived from the original silano-component by the action of water is low molecular weight having hydrophillic OH, thus, in the aqueous medium silanol is homogeneously mixed among water soluble polymer molecules. Under this condition, silanol with reacts each other stepwisely to form polysiloxane accompaning cross-linking to some extent, forming an emulsion-like sol in which water soluble polymer molecules are entangled into the newly forming cross-link networks. To obtain a stable sol, pH values ranged 2 to 5 are favorable. pH values over 5 occationally induce gelation.

One of the features of this composite sol-like solution lies on the fact that principally water-soluble polymer and polysiloxane are not chemically reacted, but entangled or intertwisted physically into crosslinked networks of newly formed polysiloxane.

In the past, some attempts have been made in which water-soluble gelatin is firstly coated, then it was crosslinked by glutaldehyde. In this case, however, the aldehyde group reacts chemically with the gelatin molecule. The significance of this invention is attributed to the fact that the water soluble polymer becomes insoluble by physical interpenetrating network entanglement, or intertwisting without chemical bonding.

The entangled water soluble polymer is no longer soluble by the formation of IPN, but as long as the polymer is not chemically modified, the polymer possesses its original characteristics. Thus heparin or gelatin possesses its biocompatibility as it is.

An interesting fact is that these molecules can be partly movable when contacted with the blood stream, in other words, the blood contact surface can be covered with a high concentration of these molecules. Another important fact is that the blood contact surface is formed of a micro-heterogeneous structure with hydrophobic (polysiloxane) and hydrophilic (water soluble polymer) domains. This structure is similar to those of blood vessels. The inventor presumes that the excellent bio-compatibility also arises from this micro-heterogeneous structure.

A preferred feature of the invention is that heparin is used as an essential ingredient and in addition to this, one or more other kind of water soluble polymer is used. The water soluble polymer including heparin is entangled into polysiloxane polymer networks in the manner as already described.

Heparin prevents the formation of blood coagulation on the inner surface of vascular prostheses or other prostheses. It delays the coagulation or makes much thinner lining. At the same time, the water soluble polymer acts as an accelerator for endothelial intimal growth.

Among water soluble polymers, bicompatible polymer such as polyethylene glycol, gelatin atelo-collagen, polyvinyl pyrrolidone, polyvinyl alcohol, polysacchride, hyaluronic acid, or chondroitin sulphate is preferably used. Polyethylene glycol is characterized by prompt absorption of albumin from blood. Polyvinyl pyrrolidone known as man-made plasma and known as excellent biocompatible polymer.

The combination of heparin and bio-compatible water soluble polymer together with polysiloxane in terms of IPN provides the way for development of useful small diameter vascular graft.

Another preferred feature of this invention is that the silico-containing solution (IPN solution) be prepared in the presence of polyvinyl alcohol. The inventor found that the long stability of the sol-like IPN solution can be obtained by the presence of polyvinyl alcohol. The reason why the solution can be effectively stabilized is not clear at present, but it is experimental fact that the sol-like IPN solution becomes very stable even after a long time elapsing. Polyvinyl alcohol prevents from precipitating the silicon component which occasionally happens in the absence of polyvinyl alcohol.

In the practical application of the present invention, heparin can be used in the form of sodium, calcium or lithium salt.

Polyethyleneglycol of molecular weight of lower than 600, is effective to give a soft-hand, and flexible nature to the vascular graft. Flake or fused mass of polyethylene glycol whose molecular weight ranges 800 to 3000 can also be used. As to polyvinyl alcohol, those of molecular weight between 300 and 5000 are preferable. Polyvinyl pyrrolidone of molecular weight of 300 to 10,000 is also preferably used. Poly-2-acrylamido-2-methylpropane sulfonic acid (or its salt) is also preferably used because of its high degree of swellability.

Treatment of this silico-containing sol-like IPN solution is not limited to vascular conduit, but is applied to other prostheses such as patches for the repair of cardiac and vascular damage, cardiac malformation, or deformity. The method for preparing the present invention may basically be achieved by contacting the vascular prostheses or other prostheses with sol-like IPN solutions, then, dried in the atmosphere containing moisture. Moisture in the air activates the silico-component, thus induces polycondensation to cross-linked polysiloxane, spontaneously entangling water soluble polymers to give IPN. Before this treatment, the vascular prostheses or other prostheses can be subjected to a glow discharge, so that affinity between the surface and the sol-like IPN solution may increase.

In the case of hydrophobic EPTFE vascular prostheses, they may be treated with tetrahydrofuran, or acetone, or alcohol beforehand to increase the wettability against the IPN solution.

Additional specific feature of this invention is that, after applying this invention, troublesome pre-clotting is no longer necessary. Blood is no longer leakable because the swollen polymer blocks infiltration of blood.

This invention is not limited to polyethylene terephthalate fabric or woven prostheses or EPTFE prostheses, the principle may be applied other prostheses made of different materials, for example, polyurethane prostheses or others.

This invention is further illustrated in and by the following examples which are given merely as illustration and are not limited to restrict in any way the scope of the invention nor the manner in which it can be practiced.

EXAMPLE 1

Preparation of IPN solution 1-(1)

Polyethyleneglycol (PEG: Mwt 6000) was dissolved in water to give a 30% solution. To this, a 30% tetrahydrofuran solution of methyl triacetoxysilane (MTAS) was carefully added dropwise. Ratio of PEG/MTAS was 3/2. After addition, pH was maintained at 3 and the reaction mixture was agitated for one hour. The resulting solution was named as solution (1-(1)).

Preparation of IPN solution 1-(2)

Polyvinylalcohol (PVA: DP=1800, Saponification degree (SPD) 99.8%) was dissolved in water to give a 20% solution. Keeping this solution at 35° C., tetrahydrofuran solution of a mixture of tetraacetoxy silane (TAS)-diacetoxy silane (DAS) (8:2), which weighs 40% based on polyvinyl alcohol used, was carefully added. pH was maintained to be 3, the solution obtained was a shade milky-white. This solution was named IPN solution (1-(2)).

Preparation of IPN solution 1-(3)

A commercial gelatin was mixed with water, then warmed up until it became a homogeneous solution. Keeping this solution at 72° C., tetrmethoxy silane (TMS)-methyltrimethoxy silane (MTMS) mixture (8:2) was added dropwise, then pH was adjusted to 2.5, under stirring. An oily silicone was separated as upper layer in the initial stage, however, by constant stirring, a viscous homogeneous sol-like solution was obtained. This was named as IPN-solution (1-(3)).

Preparation of IPN solutions 1-(4) to 1-(7)

Aqueous solutions of polyvinylalcohol, atelo-collagen, polyethylene glycol-polypropylene glycol block copolymer, and heparin were prepared respectively. To each of the solutions, a mixture of tetraethoxy silane (TES)-dimethyl diethoxy silane (DMDES) (9:1) was added under stirring. Stirring was continued until homogeneous sol-like solutions were obtained. These solutions were named as IPN solutions 1-(4), 1-(5), 1-(6), and 1-(7), respectively.

EXAMPLE 2

(Prearation of IPN solution containing heparin)

Preparation of IPN solution having heparin as an essential ingredient 2-(1).

100 parts of PVA (DP=1200, (SPD) 99.5%) and 50 parts of heparin were added to water to give a homogeneous 10% solution. After pH had been adjusted to 2.5, 300 parts of TES was added and continued to stir at 30° C. After 6 hours a homogeneous, shade milky-white solution was obtained.

In order to obtain IPN solution, it is essential to add silico-component having crosslinkability lastly. When the order of addition is not adequate or reverse, heparin molecules are not able to intertwist or entangle into cross-linked networks of polysiloxane, but exist rather as simple mixture. In this case, heparin easily releases off from the surface when practically used (see Reference example 1).

REFERENCE EXAMPLE 1

Preparation of reference IPN solution (R-1)

An aqueous 10% solution of PVA (100 parts) (DP=1200, SPD 99.5%) was adjusted to pH 2.5, then 300 parts of TES was added, and continued to stir at 30° C. until homogeneous sol-like solution was obtained. To this 50% by weight of heparin based on polyvinylalcohol was added and mixed to give a homogeneous solution. The solution was reference IPN solution (R-1).

Preparation of IPN polymer solution containing heparin 2-(2)

A 8:2 mixture of PEG (DP=4000, flake) and PEG (DP=500, liquid) was dissolved to give a 20% solution.

Heparin which corresponds 50% of total PEG was added to this under stirring to give a homogeneous solution. To this, TAS, which weighs 50% based on total PEG, was added and continued to react under stirring at pH of 3 to give homogeneous solution. This solution was named as IPN solution (2-(2))

Preparation of IPN polymer solution containing heparin 2-(3)

Except that gelatin was used in place of PEG and temperature was 70° C. and that the concentration was 0.1%, other conditions were the same as preceding example. In this case, resultant homogeneous sol-like solution was desirably kept over 50° C. until the treatment of vascular graft.

The IPN solutions obtained by Examples 1 and 2 are desirably used within 6 weeks after preparation, since occationally silicone component may separate and precipitate.

Preparation of IPN solution containing heparin 2-(4)

Experimental conditions were the same as in 2-(1) except tetrahydrofuran-water mixture (30:70) was used as solvent. This solution was IPN solution 2-(4).

EXAMPLE 3

Preparation of IPN solutions 3-(1) containing heparin, coexisting with polyvinyl alcohol (1) An aqueous solution containing 5% by weight pf PVA (DP=2000, SPD 99.5%), 5% by weight of PEG (DP=1300), and 10% by weight of heparin was adjusted to pH of 3.

To this solution, TES, which weighs 3 times of polyvinyl alcohol, was added and kept at 40° C. under vigorous stirring for four hours to give a homogeneous solution (IPN solution (3-(1))). This was found to be stable after 2 months.

(2) An aqueous solution containing 5% by weight of PVA (DP=1200, SPD 99.8%), 1% by weight of PEG (DP=550), 5% by weight of PEG (DP=1800), 8% by weight of heparin was adjusted to pH of 2. To this, a mixture of MTAS-DMDAS (7:3), weight of which was equal to the sum of the polymers used above was added dropwise and continued to agitate.

The homogeneous sol-like solution was obtained after 5 hours, which was stable after 6 weeks. This is IPN solution (3-(2)).

(3) To an aqueous solution comprising 7% by weight of polyvinylalcohol, 5% by weight of polyvinyl pyrrolidone and 7% by weight of heparin, a dioxane solution of a mixture of TAS-DMDA (1:1) at pH of 2.8 was added. The homogeneous sol-like solution was obtained by agitation. This is IPN polymer solution (3-(3)).

(4) An aqueous solution comprising 6% by weight of PVA (DP=1600), 1.5% by weight of a mixture of gelatin and atelo-collagen (1:1) and 5% by weight of heparin was maintained at 60° C. to give a homogeneous solution. To this solution, a mixture of TMS and MTMS (6:4) was added under stirring at 50° C. A homogeneous sol-like solution was obtained. This is IPN solution (3-(4)).

EXAMPLE 4

Treatment of vascular grafts made of polyethylene terephthalate with the IPN solution.

Woven and crimped vascular grafts made of polyethylene terephthalate (Tetron ®) having inner diameter of 10 mm, 4 mm, 3 mm and 2 mm respectively were prepared. The grafts were woven by use of 0.3 denier filaments and porosities were determined to be around 120 (ml/cm$^2$/120 mmHg/min).

Each of these vascular grafts was immersed in the IPN solution obtained in Examples 1, 2, and 3 for about 5 to 10 minutes, special cautions being taken so that internal surface may be sufficiently wetted, then, the IPN solution was forced to infiltrate to external surface from internal bore. After these treatments, vascular prostheses were dried in the ambient atmosphere.

EXAMPLE 5

Treatment for EPTFE vascular graft

A 1 kg of commercial tetrafluoroethylene powder (Tefron, product of Mitsuifluoro chemical Co.) and 260 ml of naphtha were mixed uniformly, and extruded in the form of tube, then naphtha was evaporated. This tube was stretched longitudinally three times the original length at about 300° C. The tube could easily extend to give fibrillated internal surface. Around the external surfaces, another stretched PTFE tape was wound to reinforce, then the graft was cured at 340° C. for 5 minutes. Thus, so called EPTFE graft was prepared. Two grafts were prepared in this way. Their inner diameter were 3 mm and 10 mm respectively. Since EPTFE graft is hydrophobic, these grafts were treated with tetrahydrofuran or acetone before being treated with the IPN solution.

During the treatment with the IPN solution, the graft may slightly pull or softly press repeatedly so that the solution may contact every portion of the fibrillated surface. The grafts after treatment were dried in the ambient atmosphere.

EXAMPLE 6

Using the grafts obtained in the Example 4, a part of iliac or femoral artery of adult dog was replaced with end to end fashion. Each experiment was made using 5 dogs, left and right legs, totaled 10 cases for each experiment. Results are summarized in the following table.

| Experiment No. | Diameter of vascular graft | Place of transplantation | Kind of IPN solution | After 3 months | After 6 months | After 1 year |
|---|---|---|---|---|---|---|
| (1) | 4 mm | iliac artery | 1 - (1) | ⊚ | ⊚ | o |
| (2) | 4 mm | " | 1 - (2) | ⊚ | ⊚ | o |
| (3) | 4 mm | " | 1 - (3) | ⊚ | ⊚ | o |
| (4) | 4 mm | " | 1 - (4) | ⊚ | ⊚ | o |
| (5) | 4 mm | " | 1 - (5) | ⊚ | ⊚ | o |
| (6) | 4 mm | " | 1 - (6) | ⊚ | ⊚ | o |
| (7) | 4 mm | " | 1 - (7) | ⊚ | ⊚ | o |
| (8) | 3 mm | femoral | 2 - (1) | ⊚ | ⊚ | o |
| (9) | 3 mm | " | 2 - (2) | ⊚ | ⊚ | o |
| (10) | 3 mm | " | 2 - (3) | ⊚ | ⊚ | o |
| (11) | 2 mm | " | 2 - (1) | ⊚ | ⊚ | o |
| (12) | 2 mm | " | 2 - (1) | ⊚ | ⊚ | o |
| (13) | 2 mm | " | 2 - (1) | ⊚ | ⊚ | o |
| (14) | 2 mm | " | 3 - (1) | ⊚ | ⊚ | o |
| (15) | 2 mm | " | 3 - (2) | ⊚ | ⊚ | o |
| (16) | 2 mm | " | 3 - (3) | ⊚ | ⊚ | o |
| (17) | 2 mm | " | R - 1 | x | x | x |
| (18) | 3 mm | " | R - 1 | o | x | x |
| (19)* | 3 mm | " | — | (—) | (—) | (—) |
| (20)* | 2 mm | " | — | (—) | (—) | (—) |

⊚ Patent over 80%,
o Patent over 60%,
x Patent lower than 60%,
(—) all occluded
*untreated, control

EXAMPLE 7

Using the vascular graft of 3 mm diameter obtained in the Example 5, a part of femoral artery of adult dog was replaced. Each experiment is run using 5 dogs (left and right legs, total ten cases). The results obtained are summarized in the following table.

| IPN-solution | Number of patency among 10 cases tested | |
|---|---|---|
| | After 3 months | After one year |
| R - (1) | 4 | 2 |
| 1 - (1) | 9 | 9 |
| 1 - (2) | 8 | 8 |
| 1 - (3) | 9 | 9 |
| 1 - (4) | 9 | 8 |
| 1 - (5) | 10 | 9 |
| 1 - (6) | 10 | 9 |
| 1 - (7) | 9 | 9 |
| 2 - (1) | 10 | 10 |
| 2 - (2) | 9 | 9 |
| 2 - (3) | 9 | 8 |
| 3 - (4) | 10 | 9 |
| 3 - (1) | 9 | 9 |
| 3 - (2) | 9 | 8 |
| 3 - (3) | 10 | 9 |
| —* | 1 | 0 |
| — | 0 | 0 |

*Control: untreated with IPN solution

EXAMPLE 8

Commercial Dacron patch and Tefron patch were treated with the IPN solution 2-(1), 2-(2), and 3-(1). These patches were transplanted in a part of descending aorta of adult dogs.

After 3 months, dogs were sacrificed and the patches were examined. In all cases, almost no coagulation was observed and endothelial growth was quite young.

On the other hand, untreated control patch had blood-coagulation which covered almost all the surface and endothelial cell growth was partly observed. The thickness of endothelial cell lining was about 1 mm.

To examine the results at the earlier period of transplantation, same experiments were performed, and removed the transplanted patch after one week. Untreated control patch had blood-coagulation on all the surface, however, treated patch with IPN solution has no blood coagulation.

REFERENCE EXAMPLE 2

Using Dacron vascular grafts treated with the IPN solution 2-(1) and R-1 (Ref. Example) releasing behavior of heparin in the water stream at 37° C. was examined. The data with time are summarized in the table below.

| | Percent released from the graft | | | | | | |
|---|---|---|---|---|---|---|---|
| | 1 day | 2 days | 4 days | 8 days | 12 days | 30 days | 90 days |
| 2 - (1) | 12% | 26% | 26% | 29% | 29% | 31% | 34% |
| R - (1) | 23% | 35% | 42% | 50% | 54% | 80% | 97% |

R-(1) is not an ideal IPN solution, therefore after one month, 80% of the original heparin was released out. However, it is notable that the solution 2-(1) which is a satisfactory IPN solution results in longtime retention of heparin (only 30% release).

What I claim is:

1. A cardiovascular prosthesis, wherein at least a part of its blood contact surface is formed by a polymer composition comprising a water soluble polymer and a crosslinked polysiloxane, at least a part of said water soluble polymer being entangled or intertwisted into polysiloxane networks.

2. A cardiovascular prosthesis according to claim 1, wherein said water soluble polymer includes heparin as an essential ingredient and at least a part of heparin as well as the other water soluble polymer component or components is entangled or intertwisted into said polysiloxane networks.

3. A cardiovascular prosthesis according to claim 2, wherein said water soluble polymer further includes polyvinyl alcohol.

4. A cardiovascular prosthesis according to claim 1, wherein said water soluble polymer comprises at least one selected from the group consisting of polyethylene glycol, polypropylene glycol, ethylene oxide-propylene oxide copolymer, polyvinyl pyrrolidone, soluble collagen, gelatin, polyacrylic acid, polymethacrylic acid, polyhydroxy-ethyl methacrylic acid, polyhydroxy ethylacrylic acid, polyacrylamide, polymethacrylamide, 2-acrylamide-2-methylpropane sulfonic acid, soluble starch, methyl cellulose, polysaccharide hyaluronic acid, chondroitin sulfate, oxidized starch and dialdehyde starch.

5. A method of producing a cardiovascular prosthesis, wherein a base body of said prosthesis is treated with a solution comprising a water soluble polymer and a silico-component which has a capability of inducing polymerization to crosslinked polysiloxane.

6. A method of producing a cardiovascular prosthesis according to claim 5, wherein said water soluble polymer includes heparin as an essential ingredient.

7. A method of producing a cardiovascular prosthesis according to claim 6, wherein said water soluble polymer further includes polyvinyl alcohol.

8. A method of producing a cardiovascular prosthesis according to claim 5, wherein said silico-component is one of the group formulated as:

$$R_n\text{—Si—}R'_{n-n}$$

where R is a hydrocarbon radical, R' is one of alkoxy, acyloxy, halogen and amino radical, and n is 0, 1 or 2.

9. A method of producing a cardiovascular prosthesis according to claim 5, wherein said silico-component is one of the group formulated as:

$$R_nR'_{3-n}\text{Si—O—SiR}_mR''_{3-m}$$

where n and m are selected from 1, 2 and 3, respectively, n+m=0, 1, 2, 3 or 4, R is a hydrocarbon radical, and R' and R'' are selected from the group capable of converting to a functional group inducing polymerization by activation.

10. A method of producing a cardiovascular prosthesis according to claim 5, wherein said silico-component is one of silane coupling agents for room temperature vulcanization.

11. A method of producing a cardiovascular prosthesis according to claim 5, wherein said water soluble polymer is at least one selected from the group consisting of polyethylene glycol, polypropylene glycol, ethylene oxide-propyleneoxide copolymer, polyvinyl pyrrolidone, soluble collagen, gelatin, polyacrylic acid, polymethacrylic acid, polyhydroxy ethyl methacrylic acid, polyhydroxy ethyl acrylic acid, polyacrylamide, polymethacrylamide, 2-acrylamide-2-methyl-propane sulfonic acid, soluble starch, methyl cellulose, polysaccharide, hyaluronic acid, chondroitin sulfate, oxidized starch or dialdehyde starch.

* * * * *

UNITED STATES PATENT AND TRADEMARK OFFICE
CERTIFICATE OF CORRECTION

PATENT NO. : 4,678,468

DATED : July 7, 1987

INVENTOR(S) : TOSHIKI HIROYOSHI

It is certified that error appears in the above-identified patent and that said Letters Patent is hereby corrected as shown below:

On the cover page, Item [73], change "Bio-Medical Co., Ltd., Japan" to --- Ube Industries, Ltd., Yamaguchi-ken, Japan ---.

Signed and Sealed this

Fifth Day of January, 1988

Attest:

DONALD J. QUIGG

*Attesting Officer*     *Commissioner of Patents and Trademarks*